United States Patent [19]

Asayama

[11] Patent Number: 4,614,175

[45] Date of Patent: Sep. 30, 1986

[54] ENGINE EXHAUST GAS RECIRCULATION CONTROL SYSTEM

[75] Inventor: Yoshiaki Asayama, Himeji, Japan

[73] Assignee: Mitsubishi Denki Kabushiki Kaisha, Tokyo, Japan

[21] Appl. No.: 685,157

[22] Filed: Dec. 21, 1984

[30] Foreign Application Priority Data

Dec. 27, 1983 [JP] Japan ................................. 58-246873
Mar. 17, 1984 [JP] Japan ................................... 59-51824

[51] Int. Cl.$^4$ ........................................... F02M 25/06
[52] U.S. Cl. ..................................... 123/571; 204/425
[58] Field of Search .............. 123/568, 571, 569, 440, 123/489, 589; 60/276, 278, 285; 204/424, 425, 426, 427, 428, 429

[56] References Cited

U.S. PATENT DOCUMENTS

| | | | |
|---|---|---|---|
| 4,005,689 | 2/1977 | Barnard ............................ | 60/278 X |
| 4,108,122 | 8/1978 | Barnard ............................ | 60/276 X |
| 4,168,683 | 9/1975 | Hata et al. ........................ | 123/571 |
| 4,272,329 | 6/1981 | Hetrick et al. ..................... | 204/1 T |
| 4,385,616 | 5/1983 | Kobayashi et al. ................ | 123/571 |
| 4,409,949 | 10/1983 | Tanaka et al. ..................... | 123/571 |
| 4,445,489 | 5/1984 | Kobayashi et al. ................ | 123/571 |
| 4,471,745 | 9/1984 | Yoshioka et al. .................. | 123/571 |

Primary Examiner—Willis R. Wolfe, Jr.
Attorney, Agent, or Firm—Leydig, Voit & Mayer, Ltd.

[57] ABSTRACT

An exhaust gas recirculation control system for an engine, in which the recirculation rate is controlled so as to have a desired value by an exhaust gas recirculation control valve disposed between the exhaust pipe and the inlet pipe of the engine. The control valve is controlled by an electronic control unit which determines the desired recirculation rate from a predetermined relationship based on the operating condition of the engine which is determined by the engine speed and the engine pressure as well as on the output of an oxygen sensor. The inlet pipe of the engine may be divided into two inlet paths, one of which has mounted thereon the oxygen sensor.

13 Claims, 9 Drawing Figures

ENGINE EXHAUST GAS RECIRCULATION CONTROL SYSTEM

BACKGROUND OF THE INVENTION

This invention relates to an exhaust gas recirculation control system for an internal combustion engine, and in particular to an exhaust gas recirculation feedback control system for an engine comprising an oxygen sensor for sensing the oxygen concentration in the inlet air for the engine in which a recirculated exhaust gas is mixed whereby the mixing rate (exhaust gas recirculation rate) of the recirculated gas is accurately controlled according to the output signal of the oxygen sensor.

It is well known in the art to perform so-called "exhaust gas recirculation" (hereinafter abbreviated as EGR) where a part of the exhaust gas is introduced onto the inlet side of an engine in order to reduce nitrogen oxides (hereinafter abbreviated as NOx) which are harmful components contained in the exhaust gas of an internal combustion engine. Since the flow rate of the recirculated exhaust gas affects the performance and fuel consumption, etc., of the engine in addition to the reduction rate of NOx, it is desired that the exhaust gas be accurately controlled according to the operating condition of the engine.

However, when an EGR control valve for controlling the flow rate of the exhaust gas is used for a long time, a large amount of a liquid material such as carbon contained in the exhaust gas becomes attached to the recirculation control valve so that the flow rate of the exhaust gas at the initial stage corresponding to the opening of the recirculation controlling valve is changed, resulting in inaccurate control.

U.S. Pat. No. 4,168,683 issued to Hata et al. on Sept. 25, 1979 discloses an EGR control system for an internal combustion engine in which a feedback control signal representing the amount of actually recirculated exhaust gas is produced by detecting the concentration of either $CO_2$ or $H_2O$ in the recirculated exhaust gas.

SUMMARY OF THE INVENTION

It is accordingly an object of the invention to provide an EGR control system for an engine with accurate control performed according to the operating condition of the engine without deterioration with age by making use of the concept that in the inlet air, the oxygen concentration is proportional to the mixing rate of the exhaust gas, i.e., the EGR rate.

In order to accomplish this object, the flow rate of the recirculated exhaust gas is controlled by an EGR control valve disposed between the exhaust pipe of the engine and the inlet pipe of the engine so that the EGR rate may assume a desired value determined by the above operating condition of the engine. The EGR control valve is controlled by an electronic control unit on the basis of the outputs of a rotational speed sensor for sensing the rotation of the engine and of a pressure sensor for sensing the pressure in the inlet pipe of the engine as well as the output of an oxygen concentration detecting device which is connected to an oxygen sensor mounted on the inlet pipe.

The electronic control unit preferably includes a memory in which EGR rates corresponding to various engine speeds and inlet gas pressures and predetermined pump currents corresponding to various EGR rates and various values of the reference voltage for the oxygen concentration detecting device as a parameter are previously stored. The electronic control unit determines from the memory a desired EGR rate corresponding to the present engine speed and inlet pipe pressure, further determines from the determined desired EGR rate a desired reference voltage for the detecting device corresponding to a preset pump current, sets the determined reference voltage in the detecting device, compares the output pump current with the preset pump current, and adjusts the opening of the control valve depending on the compared result. Alternatively, the reference voltage in the oxygen concentration detecting device may be fixed so that the pump current as a parameter assumes a desired value.

Furthermore, the inlet pipe may be divided into two inlet paths for better detection of oxygen concentration, one path of which has mounted thereon the oxygen sensor and has introduced thereinto a part of the exhaust gas while the other path of which has mounted thereon a fuel injection supply device.

BRIEF DESCRIPTION OF THE DRAWINGS

An EGR control system for an engine according to this invention will be more readily apparent from the preferred embodiments shown in the accompanying drawings in which.

Throughout the figures, the same reference numerals indicate identical or corresponding portions.

DETAILED DESCRIPTION OF THE PREFERRED EMBODIMENTS

Hereinbelow will be described in detail the preferred embodiments of an EGR control system for an engine according to this invention, with reference to the drawings.

Figure 1:
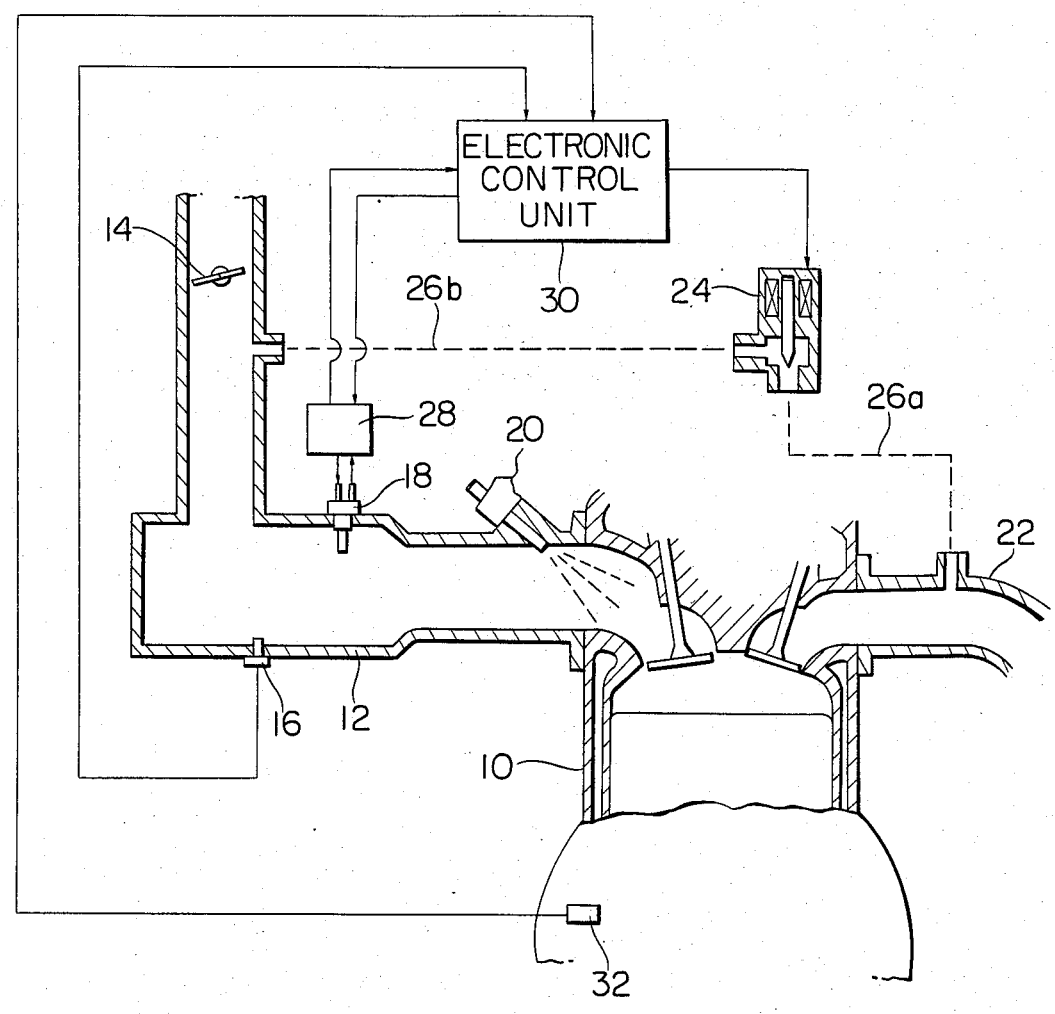
FIG. 1 shows the arrangement of a preferred embodiment of an EGR control system for an engine according to this invention.

In FIG. 1, which shows the arrangement of an EGR control system for an engine according to a first embodiment of this invention, an internal combustion engine 10 is equipped with an inlet pipe 12 which has included inside it a throttle valve 14. The inlet pipe 12 has mounted thereon a pressure sensor 16 for detecting the pressure within the inlet pipe 12, an oxygen sensor 18 for sensing the oxygen concentration in the inlet air for the engine 10 which flows through the inlet pipe 12, and a fuel injection valve 20 for supplying fuel into the inlet pipe 12. The oxygen sensor 18 is disposed on the upstream side of the fuel injection valve 20 in the inlet pipe 12 so that the fuel injected by the fuel injection valve 20 will not adversely affect the sensing performance of the oxygen sensor 18. The engine 10 is also equipped with an exhaust pipe 22. An EGR control valve 24 is disposed between pipes 26a and 26b interconnecting the inlet pipe 12 and the exhaust pipe 22, the opening of which is electromagnetically controlled so that the flow rate of an exhaust gas recirculated from the exhaust pipe 22 to the inlet pipe may assume a desired value. The oxygen sensor 18 is electrically connected to an oxygen concentration detecting device 28 which is further electrically connected to an electronic control unit 30. The electronic control unit 30 is also electrically connected to a rotational speed sensor 32 for sensing the rotational speed of the engine 10 and to the pressure sensor 16.

The electronic control unit 30 receives as inputs electrical signals from the pressure sensor 16, the oxygen concentration detecting device 28, and the rotational speed sensor 32. A control means included in the unit 30 controls the opening of the control valve 24 and a correction means also included in the unit 30 corrects the degree of opening according to the operating condition of the engine 10 determined by the above input signals so that the flow rate of the recirculated exhaust gas is controlled to the above-mentioned desired level. The electronic control unit 30 also has a function of changing a reference voltage, which will be described later, of the oxygen concentration detecting device 28 according to the above input information.

Figure 2:
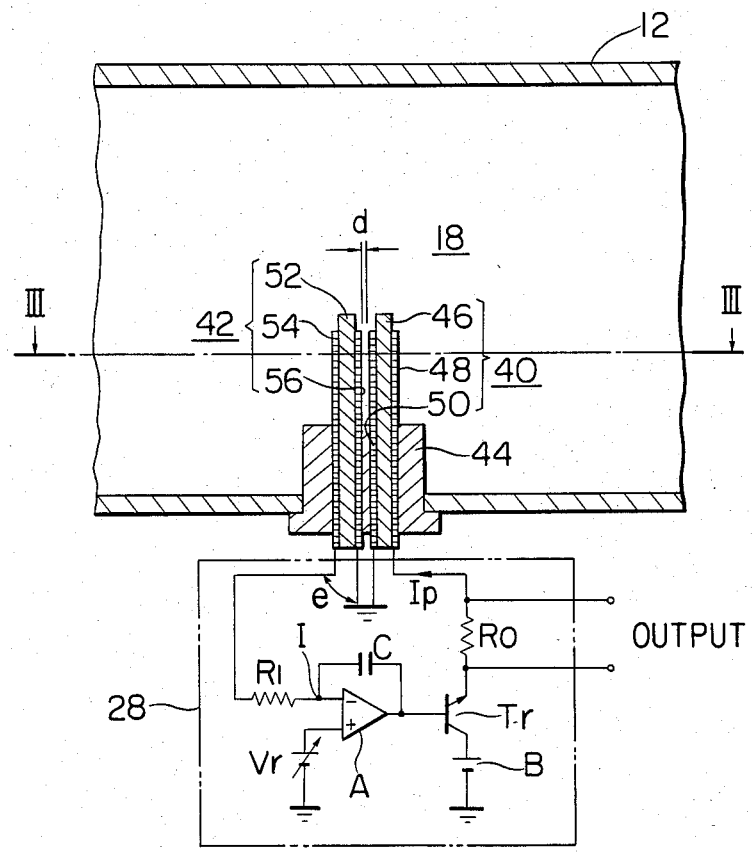
FIG. 2 shows the arrangement of the combination of an oxygen sensor and an oxygen concentration detecting device used in FIG. 1.
Figure 3:
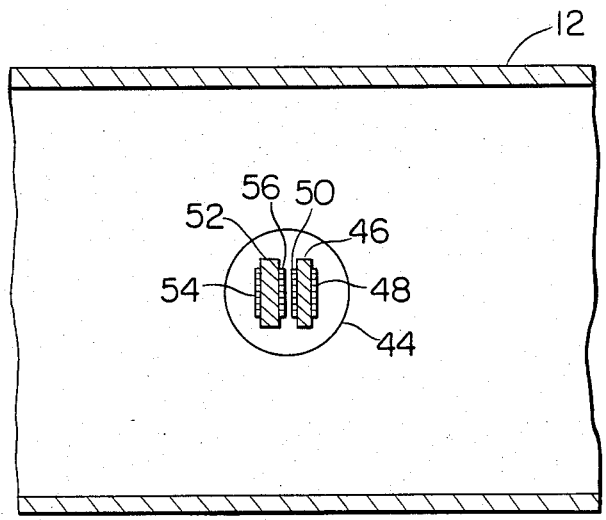
FIG. 3 shows a sectional view of the oxygen sensor taken along Line III—III in FIG. 2.

FIG. 2 shows the arrangements of the oxygen sensor 18 and the oxygen concentration detecting device 28 as described in U.S. patent application Ser. No. 606,910 filing date May 4, 1984, and FIG. 3 shows a sectional view of the oxygen sensor 18 taken along Line III—III in FIG. 2. In FIGS. 2 and 3, an oxygen sensor 18 is projecting into the inlet pipe 12 of the engine 10. This sensor 18 is formed of a solid electrolyte oxygen pump cell 40, a solid electrolyte oxygen sensor cell 42, and a supporting base 44. The solid electrolyte oxygen pump cell 40 includes an ion conductive solid electrolyte (stabilized zirconia) 46 in the form of a plate, with a thickness of about 0.5 mm, having platinum electrodes 48 and 50 disposed on opposite sides thereof. The solid electrolyte oxygen sensor cell 42, like the pump cell 40, includes an ion conductive solid electrolyte 52 in the form of a plate having platinum electrodes 54 and 56 disposed on opposite sides thereof. The supporting base 44 supports the oxygen pump cell 40 and the oxygen sensor cell 42 so that they are oppositely disposed with a minute gap "d" of about 0.1 mm therebetween.

The oxygen concentration detecting device 28 is electrically coupled to the pump cell 40 and the sensor cell 42. More specifically, the electrode 54 is connected through a resistor R1 to the inverting input of an operational amplifier A, the non-inverting input of which is grounded through a variable DC reference voltage source Vr. The electrode 48 is connected through a resistor Ro to the emitter of an NPN transistor Tr whose collector is grounded through a DC power source B and whose base is connected to the output of the operational amplifier A and the inverting input of the operational amplifier A through a capacitor C. The electrodes 50 and 56 are grounded. It is to be noted that the DC reference voltage source Vr may be of a switch-over type which can select one of a number of voltage sources. This switch-over type oxygen sensor is described in U.S. patent application Ser. No. 606,926 filed on May 4, 1984 and assigned to the same assignee as this patent application. It is also to be noted that the voltage of the variable voltage source Vr is controlled by an electrical signal from the electronic control unit 30. A different type of oxygen sensor which may be applied to this invention is disclosed in U.S. Pat. No. 4,272,329 issued to Hetrick.

The oxygen concentration detecting device 28 receives as an input an electromotive force "e" developed across the electrodes 54 and 56 of the oxygen sensor cell 42. The operational amplifier A provides as an output an electrical signal proportional to the difference between the reference voltage Vr and the voltage at input point I which is the inverting input terminal of the operational amplifier A. The output of the operational amplifier A drives the transistor Tr to control a pump current Ip flowing through the electrodes 48 and 50. The reference voltage Vr can be set to a predetermined value by the electronic control unit 30 according to the operating condition of the engine 10. The resistor Ro serves to develop thereacross an output voltage corresponding to the pump current Ip which is proportional to the oxygen concentration in the inlet air for the engine 10. Ro is preset to a desired resistance so that the pump current Ip will not be excessive in relation to the DC power source B.

Figure 4:
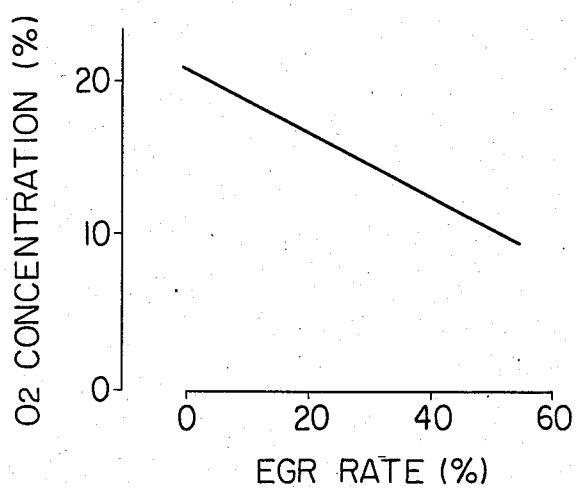
FIG. 4 shows a characteristic curve of oxygen concentration as a function of EGR rate.

FIG. 4 shows a characteristic curve of the oxygen concentration (percent) in the inlet air mixed with the recirculated exhaust gas as a function of the exhaust gas mixing rate, i.e., the EGR rate (percent). It is seen from FIG. 4 that the oxygen concentration is inversely proportional to the EGR rate.

Figure 5:
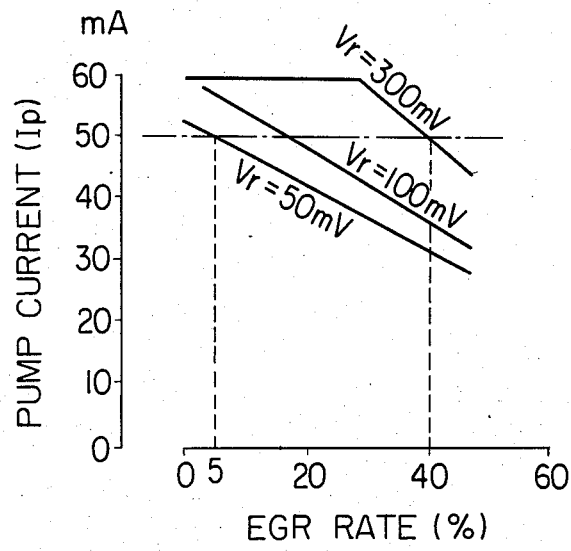
FIG. 5 shows characteristic curves of pump current as a function of EGR rate for various reference voltage levels of the oxygen concentration detecting device being a parameter.

FIG. 5 shows characteristic curves of pump current Ip (mA) as a function of EGR rate (percent). Since it is known from, e.g., the above noted U.S. Pat. No. 4,272,329 that the pump current provided as an output from the oxygen sensor is proportional to the oxygen concentration in the inlet pipe, it can be said that in FIG. 5 the oxygen concentration can be substituted for the pump current. These 3 characteristic curves indicate the variation of the pump current Ip in response to the variation of the EGR rate of the engine 10 with the reference voltage Vr being held at 50 mV, 100 mV, and 300 mV respectively. It is seen from FIG. 5 that the pump current Ip is inversely proportional to the EGR rate and that the reference voltage Vr is directly proportional to the EGR rate, supposing that the pump current Ip be fixed at a constant value, such as 50 mA.

It is to be noted that although FIG. 5 merely shows the reference voltage Vr of 50 mV, 100 mV, and 300 mV, any values between 20 to 290 mV may be used. Also, since the oxygen pump cell 40 may break down due to an excessive pump current Ip flowing therethrough, the pump current Ip is limited to 60 mA or less by the presence of the DC power source B and the resistor Ro.

The operation of the EGR control system for an engine according to this invention will now be described with reference to FIG. 6 which is a flow chart of the operations performed by the electronic control unit 30.

When the engine 10 is started, the inlet air sucked into the engine 10 is introduced from the atmosphere through an air cleaner (not shown) and the throttle valve 14 to the inlet pipe 12. On the other hand, the electronic control unit 30 determines the operating condition of the engine 10 on the basis of the electrical signals from the pressure sensor 16 and the rotational speed sensor 32 and calculates an EGR rate according to the determined operating condition. Methods of determination and calculation are well known in the art and so a detailed description thereof is omitted here.

At the initial stage, the electronic control unit 30 causes the EGR control valve 24 to open by a certain degree corresponding to the initial EGR rate as calculated above. The exhaust gas recirculated by operation of the control valve 24 is introduced into the inlet pipe 12 through the pipes 26a and 26b and is mixed with the inlet air. As the inlet air thus mixed with a part of the exhaust gas is introduced through the inlet pipe 12 into the engine 10, the oxygen sensor 18 senses the oxygen concentration in the inlet air. Namely, some of the inlet air is introduced into the minute gap "d" between the oxygen pump cell 40 and the oxygen sensor cell 42 of the oxygen sensor 18. Then, the oxygen in the gap is pumped out of the gap by the operation of the oxygen pump cell 40, which is operated by the pump current Ip. Consequently, there arises a difference in oxygen concentration between the outside and the inside of the gap, and an electromotive force "e" develops across the oxygen sensor cell 42 in proportion to the difference in oxygen concentration. This electromotive force "e" is input to the inverting input terminal of the operational amplifier A through the resistor R1. The operational amplifier A provides as an output an electrical signal corresponding to the difference between the reference voltage Vr and the voltage at the inverting input of the amplifier A. This causes the pump current Ip to flow through the resistor Ro to the oxygen pump cell 40 in proportion to the output of the operational amplifier A.

Figure 6:
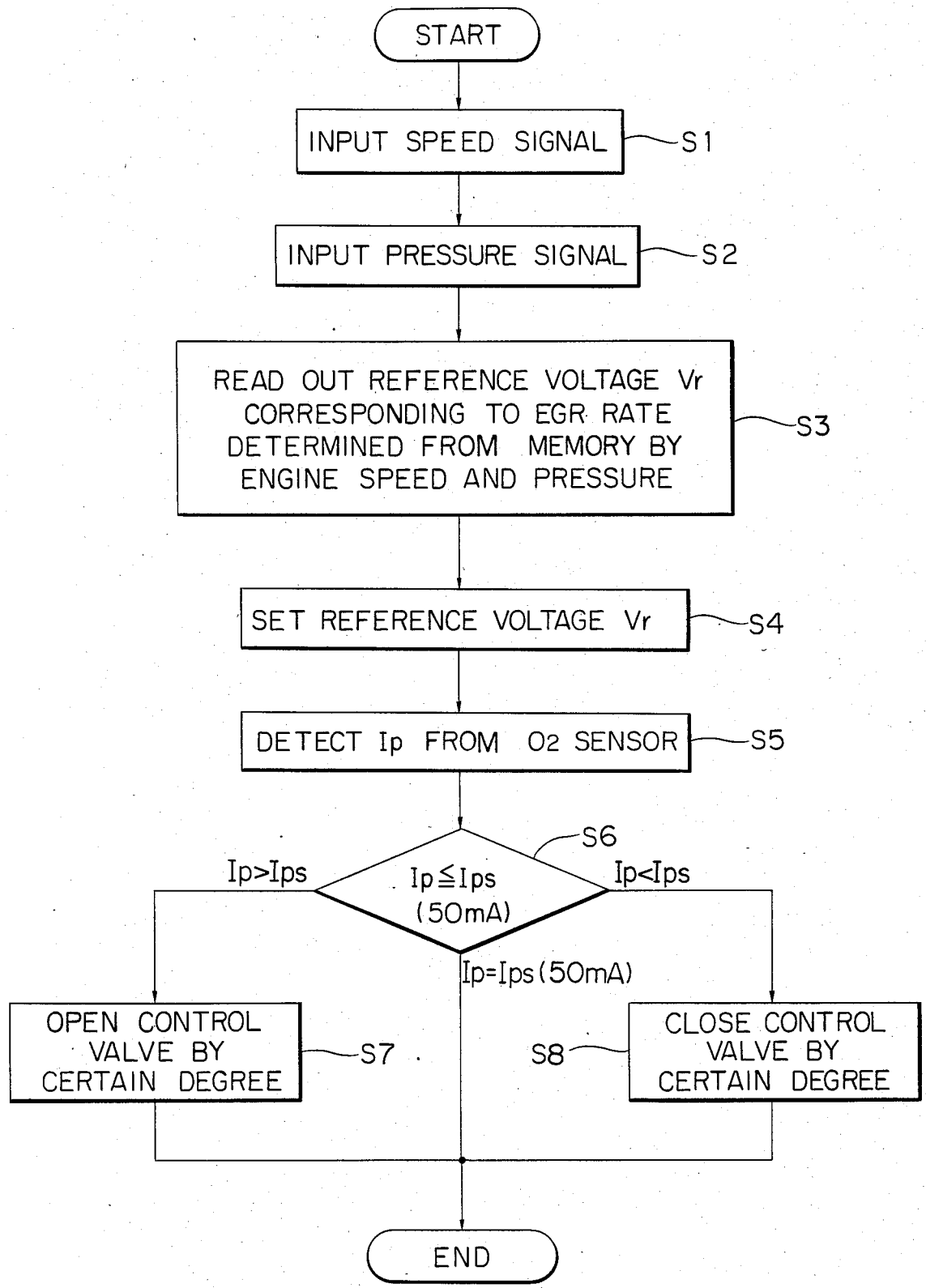
FIG. 6 shows a flow chart of processes executed by an electronic control unit used in FIG. 1 according to a first embodiment of this invention applied to the arrangement of FIG. 1.

On the other hand, when the electrical signals from the speed sensor 32 and the pressure sensor 16 are provided to the electronic control unit 30 as shown in Steps S1 and S2 in FIG. 6, a desired EGR rate is determined from data previously stored in a memory (not shown) included in the unit 30 on the basis of the operating condition of the engine 10 determined by these electrical signals, and then a desired reference voltage Vr is determined from the characteristic curves shown in FIG. 5 which are also previously stored in the memory. For example, supposing that the pump current Ip is required to be set at 50 mA, when it is found from the operating condition determined by the speed signal and the pressure signal that a desired recirculation rate is 5%, the desired reference voltage Vr is determined to be 50 mV as seen from FIG. 5. This operation is done in Step S3. After the determination of the desired reference voltage of 50 mV, the reference voltage of 50 mV is set in the oxygen concentration detecting device 28 by the electronic control unit 30 (Step S4). Therefore, correction of the opening of the control valve 24 should be made so that the pump current Ip becomes 50 mA.

Therefore, it is necessary to detect the output of the oxygen sensor 18 corresponding to the actual pump current Ip (Step S5). Then, comparison is made between the detected pump current Ip with the supposed or set pump current Ips in Step S6. If the detected pump current Ip actually flowing through the resistance Ro is larger than the set value Ips of 50 mA, it is seen from the characteristic curve in the case of 50 mA in Ip that the present EGR rate is smaller than the desired value of 5%. Therefore, the electronic control unit 30 causes the control valve 24 to open by a certain degree (Step S7). This causes the amount of recirculated exhaust gas to be increased to correspondingly increase the amount of the exhaust gas in the inlet air so that the oxygen concentration in the inlet air is reduced.

Thus, the oxygen concentration in the inlet air is reduced, thereby reducing the pump current Ip flowing through the resistor Ro to 50 mA, and thereupon it is found that the present EGR rate has now become equal to the desired value of 5%.

On the other hand, if the detected pump current Ip is less than 50 mA, the control valve 24 is closed by a certain degree (Step S8). As a result, like the above case, the EGR rate is to be controlled to the desired value of 5%.

In another case where a desired EGR rate is, for example, 40% depending upon the operating condition determined by the speed signal and the pressure signal, the reference voltage Vr may be set to 300 mA so that the pump current Ip assumes the same supposed value of 50 mA whereby the opening of the EGR control valve 24 is corrected.

While in the description of the above embodiment that the reference voltage Vr is variable and the opening of the EGR control valve 24 is controlled using feedback control so that the pump current Ip may assume a fixed value, it is also possible that the opening of the control valve 24 be controlled with the reference voltage Vr being fixed so that the EGR rate will assume a desired value by the detection of the variation of the pump current Ip, as seen also from the characteristic curves shown in FIG. 5.

Figure 7:
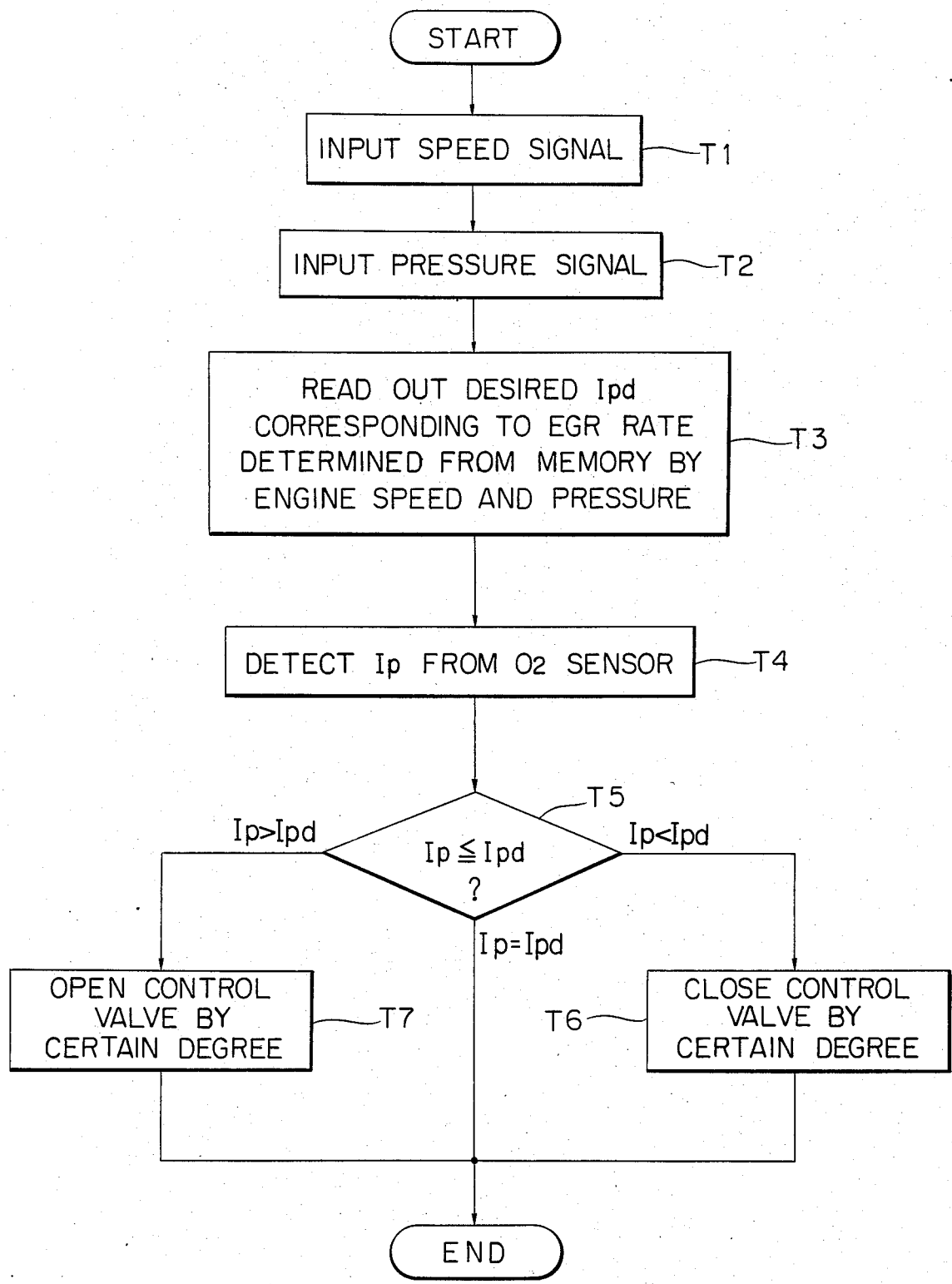
FIG. 7 shows a flow chart of processes executed by an electronic control unit used in FIG. 1 according to a second embodiment of this invention applied to the arrangement of FIG. 1.

This possible modification is made in a second embodiment of an EGR control system for an engine according to this invention, as illustrated in FIG. 7.

FIG. 7 is a flow chart of the processes executed by the electronic control unit 30 in a second embodiment of this invention. In the figure, after having obtained a speed signal and a pressure signal from the respective sensors 32 and 16 in Steps T1 and T2, Step T3 is performed in which a desired pump current Ipd corresponding to an EGR rate determined by the combination of speed data and pressure data is read out from the memory which also stores therein data of FIG. 5. Then, in Step T4, the actual pump current Ip of the oxygen sensor 18 is detected from the voltage drop across the resistor Ro in the oxygen concentration detecting device 28. This detected Ip signal is compared in Step T5 with the desired pump current Ipd as determined above. If the pump current Ip is less than the desired pump current Ipd, then in Step T6 the EGR control valve 24 is closed by a certain degree. This operation continues until the pump current Ip become equal to the desired pump current Ipd, at which point the EGR rate becomes a desired value. On the other hand, if it is found in Step T5 that the pump current Ip is larger than the desired pump current Ipd, then in Step T7 the EGR control valve 24 is opened by a certain degree. This operation also continues until the EGR rate becomes a desired value corresponding to the operating condition of the engine 10 determined by the engine speed and the engine pressure.

Figure 8:
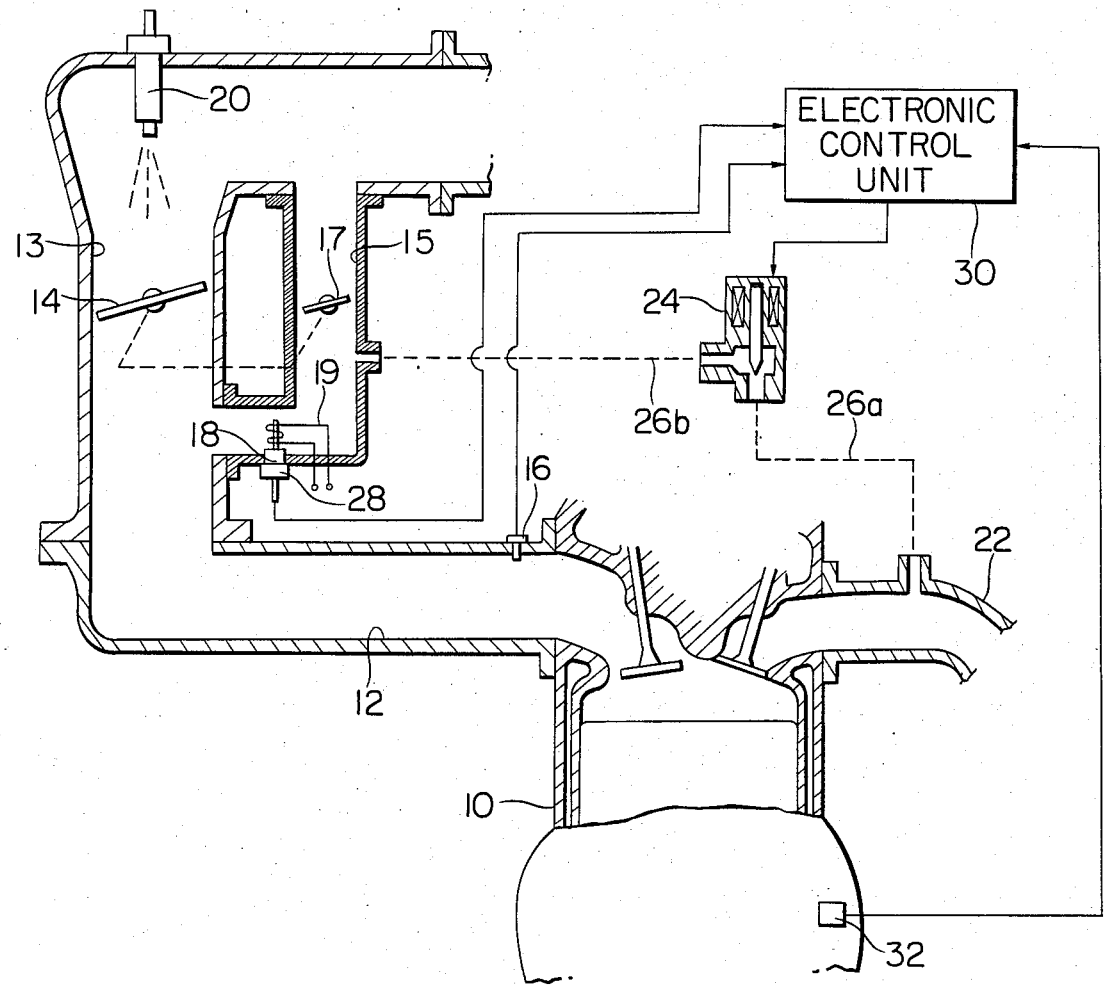
FIG. 8 shows the arrangement of another preferred embodiment of an EGR control system for an engine according to this invention; and, FIG. 9 shows characteristic curves of oxygen concentration as a function of EGR rate for the arrangement of FIG. 8.

In FIG. 8 is shown another embodiment of an EGR control system for an engine according to this invention. This embodiment is different from the embodiment shown in FIG. 1 in that the embodiment of FIG. 8 has two inlet paths 13 and 15 in which throttle valves 14 and 17 are respectively disposed. Furthermore, the oxygen sensor 18 connected to the oxygen concentration detecting device 28 projects into the inlet path 15. The oxygen sensor 18 is preferably provided with a heater 19 so that the sensor 18 is heated to a certain temperature (for example, 600 degrees or more) in which the sensor 18 is normally operated. The fuel injection valve 20 is disposed in the inlet path 13 and on the upstream side of the throttle valve 14, in contrast to the first embodiment. The electronic control unit 30 similarly receives as inputs the output signals of the oxygen concentration detecting device 28, the pressure sensor 16, and the rotational speed sensor 32, and provides an output to the control valve 24. It is to be noted that the heater 19 need not be used as in the embodiment shown in FIG. 1.

In operation, when the engine 10 is started, the inlet air flows through the inlet paths 13 and 15. The inlet air flowing through the inlet path 13 is mixed with fuel injected from the fuel injection valve 20 and the resultant mixed gas is introduced through the throttle valve 14 and the inlet pipe 12 into the engine 10. On the other hand, the inlet air flowing through the inlet path 15 passes through the throttle valve 17, is mixed with the exhaust gas recirculated from the exhaust pipe 22 through the pipes 26a, 26b and the control valve 24, and is then introduced into the engine 10.

Figure 9:
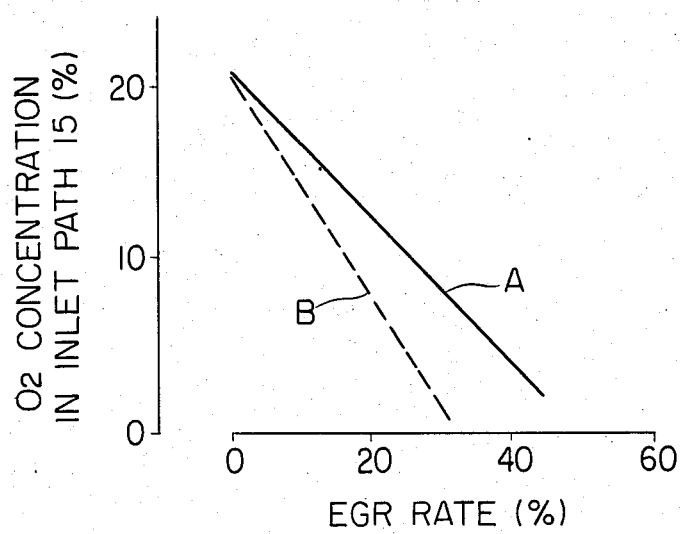

In the case where the sectional areas of the inlet paths 13 and 15 are the same, the relationship between the oxygen concentration in the inlet air mixed with the exhaust gas in the inlet path 15 and the EGR rate is illustrated in FIG. 9 by characteristic curve A. In the case where the sectional area of the inlet path 15 is half of that of the inlet path 13, the relationship between the oxygen concentration and the EGR rate is illustrated in FIG. 9 by characteristic curve B.

Thus, by mixing a part of the exhaust gas with an inlet air in the inlet path 15, and by detecting the oxygen concentration in the inlet path 15 with the oxygen sensor 18, the output characteristic of the oxygen sensor 18, i.e., the variation of the output voltage as a function of the EGR rate, becomes steep depending on the ratio of the sectional areas of the inlet paths 13 and 15, and therefore the EGR rate can be detected more sensitively.

Since the pump current is proportional to the oxygen concentration in the inlet pipe as described above, if the steep characteristic curve B in FIG. 9 is available, the characteristic curves shown in FIG. 5 also become steep so that the EGR rate can be controlled accurately without using a high sensitivity oxygen sensor.

Also in the embodiment shown in FIG. 8, the same control processes as those shown in FIGS. 6 and 7 can be executed by the same electronic control unit 30. Therefore, this invention further provides a third and a fourth embodiment illustrated by the flow charts of FIGS. 6 and 7, providing more sensitive control.

As set forth in the above, by utilizing an oxygen sensor for sensing the oxygen concentration in the inlet air mixed with a part of the exhaust gas of the engine, this invention performs feedback control so that the output of the oxygen sensor may assume a desired value to provide a desired EGR rate. Therefore, even if the EGR control valve deteriorates, the EGR control system of this invention can recirculate the exhaust gas with good precision. In addition, since the inlet pipe of the engine which is divided into two paths is used and an oxygen sensor is mounted on one of the paths to detect the oxygen concentration in the inlet air mixed with a part of the exhaust gas and to control the EGR rate according to the output of the oxygen sensor, more precise EGR detection and control are realized. Furthermore, if a fuel injection valve or a fuel supply device is disposed in the inlet path 13 as shown in the embodiment of FIG. 8, the fuel supplied by the fuel supply device does not directly fall onto the oxygen sensor held at a high temperature so that there is no possibility of the fuel being ignited and the variation of the output of the oxygen sensor due to the fuel vapor can be eliminated.

It is to be noted that while this invention has been described with respect to the above preferred embodiments, it is not limited to those embodiments but can be variously modified without departing from the spirit of this invention.

I claim:

1. An exhaust gas recirculation control system for an engine comprising:

a rotational speed sensor for sensing rotational speed of the engine;

a pressure sensor for sensing pressure in an inlet pipe of the engine;

an exhaust gas recirculation control valve for controlling an amount of exhaust gas recirculated from an exhaust pipe of the engine to the inlet pipe;

an oxygen sensing means including an oxygen sensor and an oxygen concentration detecting device for sensing oxygen concentration of a gas mixture of inlet air flowing in the inlet pipe and said recirculated exhaust gas, said oxygen sensor having a solid electrolyte oxygen pump cell and a solid electrolyte oxygen sensor cell, and said detecting device having comparing means for comparing an electromotive force developed across said oxygen sensor cell with a variable reference voltage to provide an error output therebetween, and pump current supply means responsive to said error output for supplying a pump current to said oxygen pump cell, and means for providing as an output of said detecting device a pump current signal corresponding to said pump current;

said control means including a memory for storing a plurality of exhaust gas recirculation rates corresponding to various engine speeds and engine pressures and predetermined pump currents corresponding to various exhaust gas recirculation rates and various values of said reference voltage, said control means including means for determining from said memory a desired exhaust gas recirculation rate corresponding to a particular engine speed and pressure detected by said speed and pressure sensors, for providing from said memory a desired pump current signal corresponding to said desired exhaust gas recirculation rate, for comparing the output pump current signal from said detection device with said desired pump current signal provided from said memory, and for adjusting opening of said control valve to vary the recirculation rate depending on the result of said comparing.

2. An exhaust gas recirculation control system for an engine comprising:

a rotational speed sensor for sensing rotational speed of the engine;

a pressure sensor for sensing pressure in an inlet pipe of the engine;

an exhaust gas recirculation control valve for controlling an amount of exhaust gas recirculated from an exhaust pipe of the engine to the inlet pipe;

an oxygen sensing means including an oxygen sensor and an oxygen concentration detecting device for sensing oxygen concentration of a gas mixture of inlet air flowing in the inlet pipe and said recirculated exhaust gas, said oxygen sensor including an oxygen pump cell, pump current supply means, and means providing an output pump current signal corresponsing to said pump current; and control means responsive to said oxygen sensing means for controlling opening of said exhaust gas recirculation control valve to recirculate said exhaust gas at a desired recirculation rate determined by said engine speed and said inlet pipe pressure;

said control means including a memory for storing a plurality of exhaust gas recirculation rates corresponding to various engine speeds and inlet pipe pressures and predetermined pump currents corresponding to various exhaust gas recirculation rates and various values of said reference voltage, said control means including means for determining from said memory a desired exhaust gas recirculation rate corresponding to a particular engine speed and pressure detected by said speed and pressure sensors, for providing from said memory a desired pump current signal corresponding to a a preset reference voltage for said detecting device, for comparing the output pump current signal with said desired pump current signal provided from said memory, and for adjusting opening of said control valve depending on the result of said comparing.

3. An exhaust gas recirculation control system for an engine comprising:

a rotational speed sensor for sensing rotational speed of the engine;

a pressure sensor for sensing pressure in an inlet pipe of the engine;

an exhaust gas recirculation control valve for controlling an amount of exhaust gas recirculated from an exhaust pipe of the engine to the inlet pipe;

an oxygen sensing means including an oxygen sensor and an oxygen concentration detecting device for sensing oxygen concentration of a gas mixture of inlet air flowing in the inlet pipe and said recirculated exhaust gas, said inlet pipe being divided into first and second inlet paths parallel to each other, said first inlet path having mounted thereon said oxygen sensing means;

said oxygen sensor having a solid electrolyte oxygen pump cell and a solid electrolyte oxygen sensor cell, and said detecting device having comparing means for comparing an electromotive force developed across said oxygen sensor cell with a variable reference voltage to provide an error output therebetween, pump current supply means responsive to said error output for supplying a pump current to said oxygen pump cell, and means providing as an output of said oxygen concentration detecting device an output pump current signal corresponding to said pump current; and control means responsive to said oxygen sensing means for controlling opening of said exhaust gas recirculation control valve to recirculate said exhaust gas at a desired recirculation rate determined by said engine speed and said inlet pipe pressure;

said control means including a memory for storing a plurality of exhaust gas recirculation rates corresponding to various engine speeds and engine pressures and predetermined pump currents corresponding to various exhaust gas recirculation rates and various values of said reference voltage, said control means including means for determining from said memory a desired exhaust gas recirculation rate corresponding to a particular engine speed and pressure detected by said speed and pressure sensors, for providing from said memory a desired pump current signal corresponding to a predetermined reference voltage for comparing the output pump current signal with said desired pump current signal from said memory, and for adjusting opening of said control valve depending on the result of said comparing.

4. An exhaust gas recirculation control system for an engine comprising:

a rotational speed sensor for sensing rotational speed of the engine;

a pressure sensor for sensing pressure in an inlet pipe of the engine;

an exhaust gas recirculation control valve for controlling an amount of exhaust gas recirculated from an exhaust pipe of the engine to the inlet pipe;

an oxygen sensing means including an oxygen sensor and an oxygen concentration detecting device for sensing oxygen concentration of a gas mixture of inlet air flowing in the inlet pipe and said recirculated exhaust gas, said inlet pipe being divided into first and second inlet paths parallel to each other, said first inlet path having mounted thereon said oxygen sensing means;

said oxygen sensor having a solid electrolyte oxygen pump cell and a solid electrolyte oxygen sensor cell, and said detecting device having comparing means for comparing an electromotive force developed across said oxygen sensor cell with a fixed reference voltage to provide an error output therebetween, and pump current supply means responsive to said error output for supplying a pump current to said oxygen pump cell to provide as an output of said oxygen concentration detecting device an output pump current signal corresponding to said pump current; and control means responsive to said oxygen sensing means for controlling opening of said exhaust gas recirculation valve to recirculate said exhaust gas at a desired recirculation rate determined by said engine speed and inlet pipe pressure;

said control means including a memory for storing a plurality of exhaust gas recirculation rates corresponding to various engine speeds and engine pressures and predetermined pump currents corresponding to various exhaust gas recirculation rates and various values of said reference voltage, said control means including means for determining from said memory a desired exhaust gas recirculation rate corresponding to a particular engine speed and pressure detected by said speed and pressure sensors, for providing a desired pump current signal corresponding to a preset reference voltage for said detecting device, for comparing the output pump current signal with said desired pump current signal from said memory, and for adjusting the opening of said control valve depending on the result of said comparing.

5. An exhaust gas recirculation control system for an engine comprising:
   a rotational speed sensor for sensing rotational speed of the engine;
   a pressure sensor for sensing pressure in an inlet pipe of the engine;
   an exhaust gas recirculation control valve for controlling an amount of exhaust gas recirculated from an exhaust pipe of the engine to the inlet pipe;
   an oxygen sensing means for sensing oxygen concentration of a gas mixture of inlet air flowing in the inlet pipe and said recirculated exhaust gas; and
   control means responsive to said oxygen sensing means for controlling opening of said exhaust gas recirculation control valve to recirculate said exhaust gas at a recirculation rate predetermined according to the engine speed and inlet pipe pressure sensed by said sensors.

6. An exhaust gas recirculation control system for an engine according to claim 1 further including memory means for storing predetermined recirculation rates corresponding to various engine speeds and inlet pressures.

7. An exhaust gas recirculation control system for an engine according to claim 5 wherein said oxygen sensing means comprises an oxygen sensor and an oxygen concentration detecting device.

8. An exhaust gas recirculation control system for an engine according to claim 7 wherein said oxygen sensor includes a solid electrolyte oxygen pump cell and a solid electrolyte oxygen sensor cell, and said detecting device includes comparing means for comparing an electromotive force developed across said oxygen sensor cell with a variable reference voltage to provide an error output therebetween, and pump current supply means, responsive to said error output, for supplying a pump current to said oxygen pump cell and for providing as the output of said detecting device a pump current signal corresponding to said pump current.

9. An exhaust gas recirculation control system for an engine according to claim 7 wherein said oxygen sensor includes a solid electrolyte oxygen pump cell and a solid electrolyte oxygen sensor cell, and said detecting device includes comparing means for comparing an electromotive force developed across said oxygen sensor cell with a fixed reference voltage to provide an error output therebetween, and pump current supply means, responsive to said error output, for supplying a pump current to said oxygen pump cell and for providing as the output of said detecting device a pump current signal corresponding to said pump current.

10. An exhaust gas recirculation control system for an engine according to claim 7, said engine having a inlet pipe divided into first and second inlet paths parallel to each other, said first inlet path having mounted thereon said oxygen sensing means and having introduced thereinto a part of said exhaust gas through said control valve.

11. An exhaust gas recirculation control system for an engine according to claim 10 wherein said oxygen sensor includes a solid electrolyte oxygen pump cell and a solid electrolyte oxygen sensor cell, and said detecting device includes comparing means for comparing an electromotive force developed across said oxygen sensor cell with a variable reference voltage to provide an error output therebetween, and pump current supply means, responsive to said error output, for supplying a pump current to said oxygen pump cell and for providing as the output of said oxygen concentration detecting device a pump current signal corresponding to said pump current.

12. An exhaust gas recirculation control system for an engine according to claim 10 wherein said oxygen sensor includes a solid electrolyte oxygen pump cell and a solid electrolyte oxygen sensor cell, and said detecting device includes comparing means for comparing an electromotive force developed across said oxygen sensor cell with a fixed reference voltage to provide an error output therebetween, and pump current supply means, responsive to said error output, for supplying a pump current to said oxygen pump cell and for providing as the output of said oxygen concentration detecting device a pump current signal corresponding to said pump current.

13. An exhaust gas recirculation control system for an engine according to claim 10 wherein said second inlet path has mounted thereon a fuel injection supply device.

* * * * *